United States Patent [19]

Kaneda et al.

[11] Patent Number: 5,603,714
[45] Date of Patent: Feb. 18, 1997

[54] INSTRUMENT FOR ANTERIOR CORRECTION OF SCOLIOSIS OR THE LIKE

[75] Inventors: Kiyoshi Kaneda, Sapporo; Shoichi Takahashi, Tokyo-to; Yoshiharu Asai, Gosen; Takao Shimizu, Tokorozawa, all of Japan

[73] Assignee: Mizuho Ika Kogyo Kabushiki Kaisha, Tokyo-To, Japan

[21] Appl. No.: 353,886

[22] Filed: Dec. 12, 1994

[51] Int. Cl.⁶ .................................................. A61B 17/56
[52] U.S. Cl. .................................. 606/61; 606/60; 606/73
[58] Field of Search ........................ 606/60, 61, 69, 606/70, 71, 72, 73

[56] References Cited

U.S. PATENT DOCUMENTS

| | | | |
|---|---|---|---|
| 4,041,939 | 8/1977 | Hall | 606/61 |
| 4,047,524 | 9/1977 | Hall | 606/61 |
| 5,067,955 | 11/1991 | Cotrel | 606/73 |
| 5,176,680 | 1/1993 | Vignaud et al. | 606/73 |
| 5,226,766 | 7/1993 | Lasner | 606/73 |
| 5,330,473 | 7/1994 | Howland | 606/61 |
| 5,374,267 | 12/1994 | Siegal | 606/61 |
| 5,437,669 | 8/1995 | Yuan et al. | 606/61 |
| 5,486,174 | 1/1996 | Fournet-Fayard et al. | 606/61 |

*Primary Examiner*—Michael Powell Buiz
*Assistant Examiner*—Mark S. Leonardo
*Attorney, Agent, or Firm*—Ladas & Parry

[57] ABSTRACT

For the purpose of facilitating correction of front-to-back and lateral vertebra curvature in scoliosis and the like, vertebra screws are passed through vertebra plates with spikes that dig into the sides of vertebrae and are screwed into each vertebra. The vertebra screws have rod passage holes in their heads, respectively, which holes are partially open on the side. A screw hole is provided at the top surface of each head. Rods are inserted into and passed through all the rod passage holes via the side openings in the heads of all the vertebra screws, the set-screws being each screwed into screw hole formed in the top surface of the head of the vertebra screw for the purpose of fixing the rods to the vertebra screws.

15 Claims, 7 Drawing Sheets

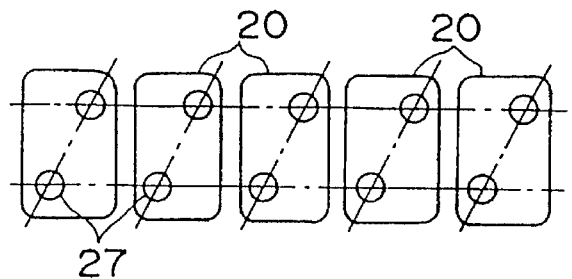
F I G. 13
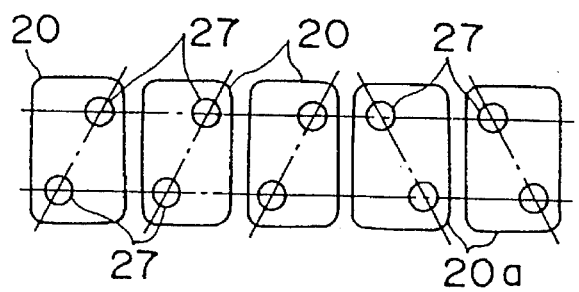
F I G. 14
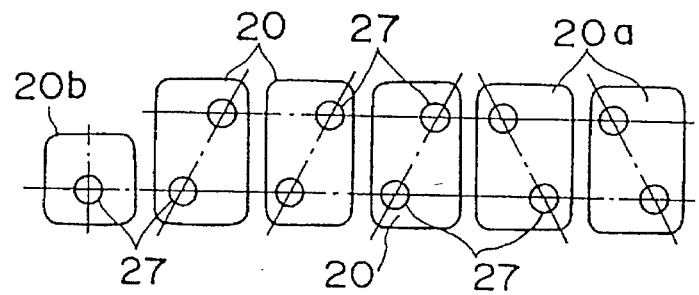
F I G. 15
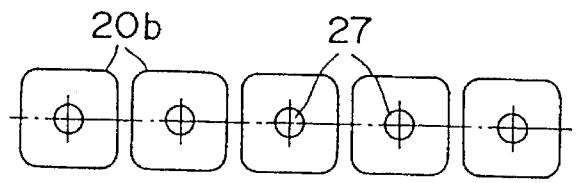
F I G. 16

INSTRUMENT FOR ANTERIOR CORRECTION OF SCOLIOSIS OR THE LIKE

BACKGROUND OF THE INVENTION

The present invention relates to an instrument for the anterior correction of such conditions as scoliosis, in which there is twisting or bending of the vertebrae of the patient.

For example, the spine of a scoliosis patient exhibits bending into a bow shape by virtue of 3-dimensional twisting, and to correct the twisting and bending of the patient's vertebrae, it is necessary to correct not only the front-to-back curvature but the left-to-right curvature of the vertebrae making up the patient's spine.

Surgical means of treatment to correct vertebral twisting and bending in a scoliosis patient include the anterior correction method in which correction of the vertebrae is performed from the side (or, in medical terms, from the anterior), and the posterior correction method in which correction of the vertebrae is performed from the rear. The method of correcting twisting and bending of vertebrae of a scoliosis patient is applied not only to the usual scoliosis patients, but also in the treatment of damaged or chipped vertebrae or laterally slipped vertebrae caused by either accidents or tumors. Treatment in the case of scoliosis involves a large number of vertebrae to be treated, the treatment being applied across a large number of vertebrae.

A known treatment instrument used to perform anterior correction for the purpose of treatment in the case of damaged vertebrae or in the case of tumors will be described later in detail. This known treatment instrument comprises a pair of vertebra plates having spikes, vertebra screws which are screwed into the vertebrae through two holes provided in the top plate of each vertebra plate, two screw rods which link the vertebra screws in a pair, and holding nuts which fix the screw rods to the vertebra screw, the vertebra screws being formed by a head part, which has a rod hole, and a threaded shank, which is formed integral with the head part.

The mounting of the above treatment instrument to the patient is done by positioning the pair of vertebra plates with the spikes on the sides of the normal vertebrae before and after a vertebra which is damaged or chipped, and screwing the vertebra screws into each of the normal vertebrae through the two holes provided in the vertebra plate top plates. The vertebra plates are positioned by passing the screw rods through the holes provided in the heads of the vertebra screws which are screwed into the two normal vertebrae adjoining the damaged or chipped vertebra, and by adjusting the holding nuts to hold the screw rods to the heads of the vertebra screws. In doing this, because the screw rod is highly rigid and is in the form of a straight line, the insertion of the screw rods into the rod holes provided in the heads of the vertebra screws can only be done if the rod holes provided in the heads of the vertebra screws are aligned along one and the same straight line. Once the treatment instrument is mounted to the patient, the damaged or chipped vertebra or intervertebral disc is removed, a different bone or ceramic bone being inserted in that location to treat a patient with a damaged or chipped vertebra caused by an accident or a tumor.

In the above-noted treatment instrument, to link the two normal vertebrae adjoining a damaged or chipped vertebra, screw rods are passed through rod holes in the heads of vertebra screws of the normal vertebrae. The screw rods are highly rigid and in the form of a straight line, so that if the two normal vertebrae are positioned along a straight line, the hole in one vertebra screw provided in one normal vertebra will be along the same straight line as the hole in the other vertebra screw provided in the other normal vertebra. Therefore, there will be no interference with the task of passing the screw rod through the rod hole in the vertebra screw provided at one normal vertebra and then through the rod hole in the vertebra provided at the other normal vertebra.

However, it is normal for the vertebrae of a scoliosis patient to be twisted and bent, and located along a curved line, so that the vertebra screws provided at the vertebrae which exhibit front-to-back curvature and lateral curvature are located along a curved line, rather than a straight line. Therefore, the rod holes provided in the heads of the vertebra screws provided at the vertebrae are located along a curved line, making it impossible to perform the task of passing the highly rigid linear screw rod through the holes in the heads of the vertebra screws. Also, to hold the screw rods to the vertebra screws, it is necessary to adjust two holding nuts while screwing them onto each vertebra screw, making this task a troublesome and time-consuming and impractical one to perform in an operating room.

SUMMARY OF THE INVENTION

The present invention was made to solve the above-described difficulties, and has as an object the provision of an anterior correction instrument for correcting scoliosis or the like, which enables reliable and easy mounting.

An anterior correction instrument for scoliosis or the like according to the present invention has a plurality of vertebra plates which have a spike on their outer edge and a hole in their top plates and which are each located at the sides of each vertebra. Vertebra screws are provided each having a partial opening in its head, the partial opening forming a rod passage hole. A screw hole is provided in the top surface of the head. The vertebra screw is passed through the hole in the top plate part of the vertebra plate and screwed into the vertebra so that each vertebra plate is held to the side of a vertebra. A rod is passed through the above-noted rod passage holes provided in the heads of the Vertebra screws which pass through each vertebra plate and are screwed into each vertebra. A set-screw is screwed into the hole provided in the top surface of the head of the vertebra screw, for fixing the rod passed through the rod passage holes to the vertebra screws.

In the anterior correction instrument according to the present invention, two diagonally opposite holes may be provided in the top plate of the vertebra plate, and a jaw may be provided at the edge of the opening of the vertebra screw to prevent the rod from jumping out. The diameter of the set-screw may be larger than the diameter of the rod.

In the vertebra screw device of the present invention, a rod passage hole is provided in the top surface of the vertebra screw head and a set-screw is screwed toward the rod passage hole. The axis of the set-screw may be in line with the axis of the shank of the vertebra screw. The axis of a screw hole provided in the top surface of the head may be in the same plane with the axis of the rod which is positioned within the rod passage hole.

The anterior correction instrument according to the present invention can also be applied to the treatment of damaged or communited fractures and to the treatment of an osteoma.

Using the anterior correction instrument according to the present invention, vertebra correction of front-to-back curvature and lateral curvature is performed by inserting the rod in the partial openings provided in the rod passage holes provided in the heads of the vertebra screws, the rod located within the rod passage holes being fixed in place by set-screws which are screwed into the holes provided in the top surfaces of the vertebra screws, for correcting twisting and curving of the vertebrae of a patient having scoliosis.

By providing a jaw at the edge of the holes in the vertebra screws, it is possible to prevent the rod from falling out of the heads of the vertebra screws, even if the rod is turned within the rod passage holes. In addition, by making the diameter of the set-screws larger than the diameter of the rod, it is possible to hold the rod securely within the rod passage holes.

In the vertebra screw device of the present invention, it is possible to reliably hold the rod within the rod passage holes by shifting the axis of the rod which is positioned within the rod passage holes from the axis of the shank of the vertebra screw toward the open side of the hole.

BRIEF DESCRIPTION OF THE DRAWINGS

FIG. 13 is a view which shows an arrangement of vertebra plates;

FIG. 14 is a view which shows another arrangement of vertebra plates;

FIG. 15 is a view which shows a further arrangement of vertebra plates;

FIG. 16 is a view which shows a still further arrangement of vertebra plates;

DESCRIPTION OF THE PREFERRED EMBODIMENTS

Before describing preferred embodiments of the present invention, to achieve a better understanding of the features of the present invention, the above-noted prior art anterior correction instrument and its associated problems will be described.

Figure 20:
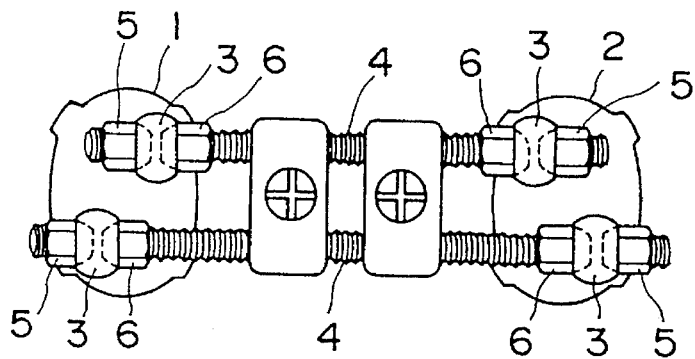
FIG. 20 is a top view showing configuration of a treatment instrument of the prior art.
Figure 21:
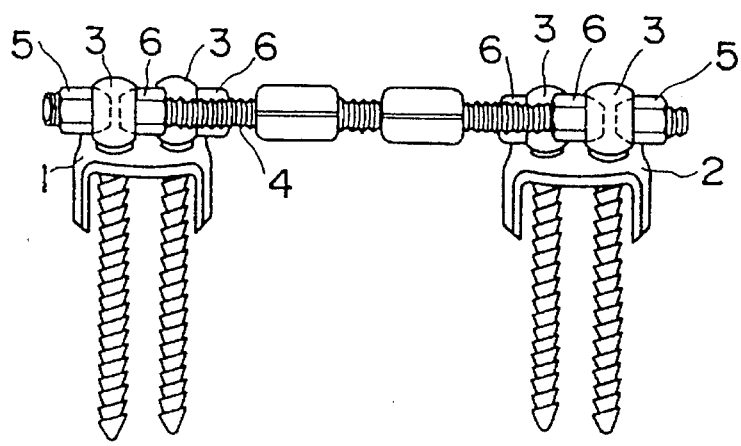
FIG. 21 is a perspective view showing the configuration of a treatment instrument of the prior art.
Figure 22:
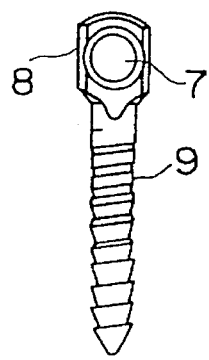
FIG. 22 is a view showing a vertebra screw of a treatment instrument of the prior art.

An example of a prior art treatment instrument used with the anterior correction method for the purpose of treating vertebral damage, tumors, and the like is shown in FIGS. 20 and 21. This treatment instrument has a pair of spiked vertebra plates 1 and 2, vertebra screws 3 and 3 which are screwed into the vertebrae through two holes provided in the top plate of each vertebra plate, two screw rods 4 and 4, which link the vertebra screws 3 and 3 provided in the vertebra plates 1 and 2 which form a pair, and holding nuts 5 and 6 which hold the screw rods 4 to the vertebra screw. Each vertebra screw 3 comprises a head part 8 having a rod hole 7, and a threaded part 9 integraly formed with this head part.

Figure 19:
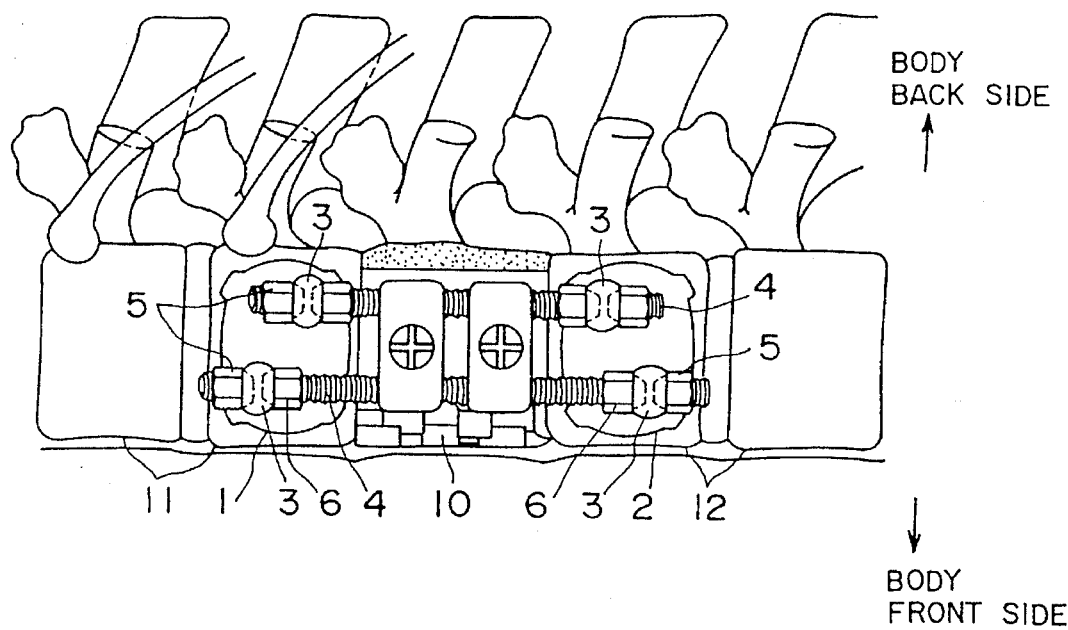
FIG. 19 is a view which shows the arrangement of a prior art treatment instrument on the sides of vertebrae.

As shown in FIG. 19, the mounting of the above-noted treatment instrument to a patient is done by positioning a pair of spiked vertebra plates 1 and 2 on the sides of the normal vertebrae 11 and 12 before and after of the vertebrae 10 which have received damage or a chipped, and by screwing the vertebra screws 3 into the normal vertebrae 11 and 12 respectively through the two holes provided in the top plates of the vertebra plates 1 and 2. The vertebra plates 1 and 2 are positioned by passing the screw rods 4 through the rod holes 7 in the heads 8 of the vertebra screws 3 which are screwed into the two normal vertebrae 11 and 12 on the sides of the damaged or chipped vertebrae 10, and by adjusting the holding nuts 5 and 6 which are screwed onto the screw rods 4 respectively to hold the screw rods 4 to the heads 8 of the vertebra screws. In doing this, because the screw rods 4 are highly rigid and are in the form of a straight line, the insertion of the screw rods 4 into the rod holes 7 in the heads 8 of the vertebra screws 3 can only be done if the rod holes 7 in the heads 8 of the vertebra screws 3 are aligned along one and the same straight line. Once the treatment instrument is mounted to the patient, the damaged or chipped vertebra 10 and intervertebral disc are removed, and a different bone or ceramic bone is inserted in that location to treat a patient with a damaged or chipped vertebra caused by an accident or a tumor.

In the above-noted treatment instrument, to link the two normal vertebrae 11 and 12 between which the damaged or chipped vertebra 10 is positioned, screw rods 4 are passed through rod holes 7 in the heads 8 of vertebra screws 3 provided at the normal vertebrae. The screw rods 4 are highly rigid and in the form of a straight line, so that if the two normal vertebrae 11 and 12 are positioned along a straight line, the hole in one vertebra screw 3 provided in one normal vertebra 11 will be along the same straight line as the hole 3 in the other vertebra screw 3 provided in the other normal vertebra 12. Therefore, there will be no interference with the task of passing the screw rods 4 through the rod holes 7 in the vertebra screw 3 provided at one normal vertebra 11 and then through the rod hole 7 in the vertebra provided at the other normal vertebra 12.

However, it is normal for the vertebrae of a scoliosis patient to be twisted and bent., and located along a curved line, so that the vertebra screws provided at the vertebrae which exhibit front-to-back curvature and lateral curvature are located along a curved line, rather than a straight line. Therefore, the problems described earlier arise. The present invention solves these problems.

Figure 1:
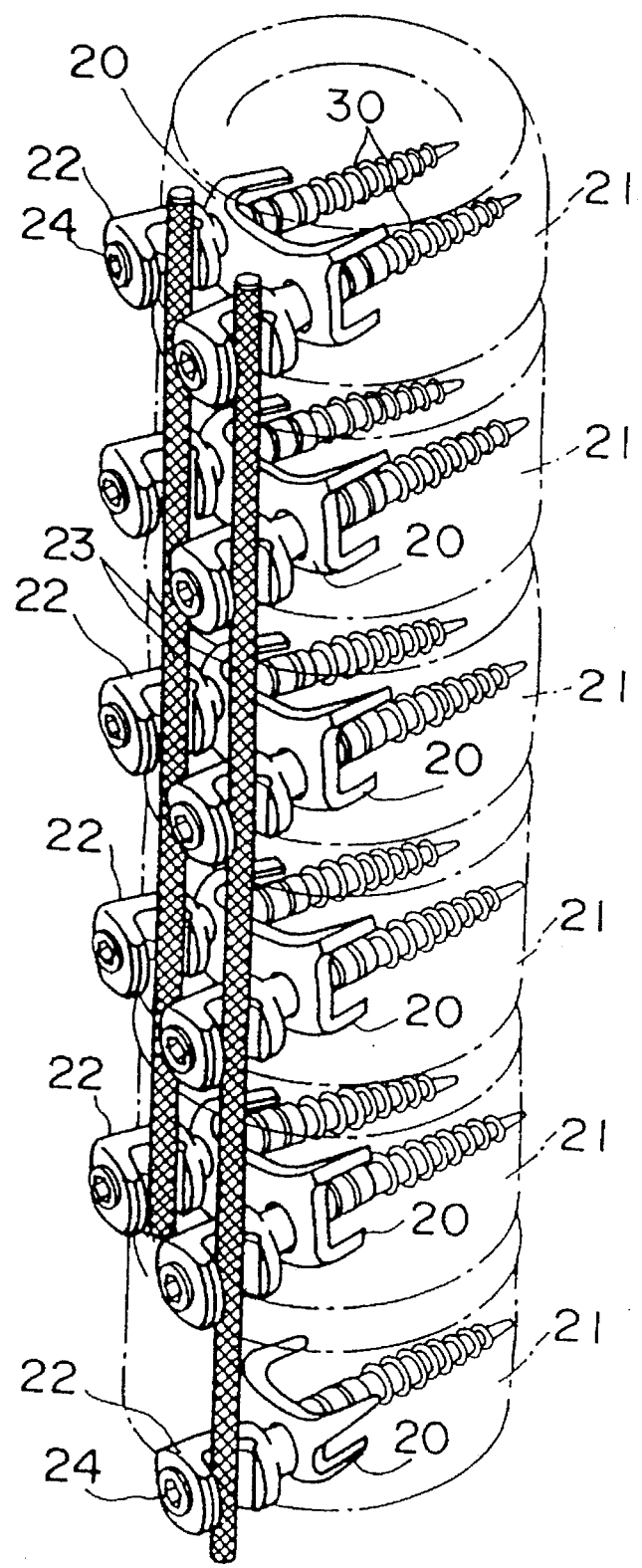
FIG. 1 is a view showing an anterior correction instrument for scoliosis or the like according to the present invention, as it is mounted to the side of the vertebrae of a patient having scoliosis.

FIG. 1 shows the condition of an anterior correction instrument according to the present invention as mounted to the vertebrae of a patient with scoliosis or the like. The anterior correction instrument according to the present invention has a plurality of vertebra plates 20, vertebra screws 22 which pass through each vertebra plate 20 and are screwed into the vertebrae 21, rods 23 linking the vertebra screws 22 which are screwed into vertebrae 21 to each other, and set-screws 24 which are provided at the top surfaces of the vertebra screws 22.

Figure 2:
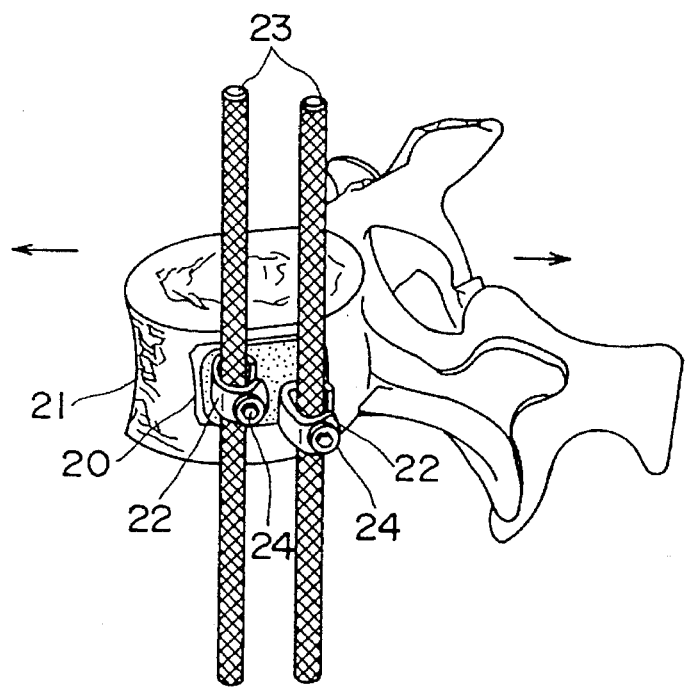
FIG. 2 is a view showing the manner in which a vertebra plate and vertebra screw are buried into the side of the vertebra.
Figure 4:
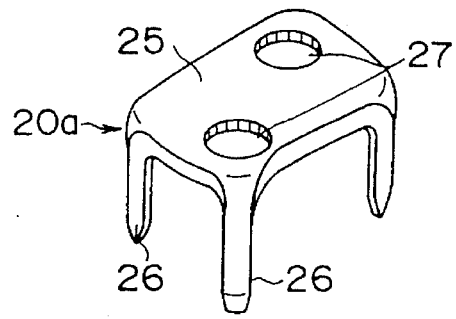
FIG. 4 is a view showing a variation of the shape of a vertebra plate.
Figure 5:
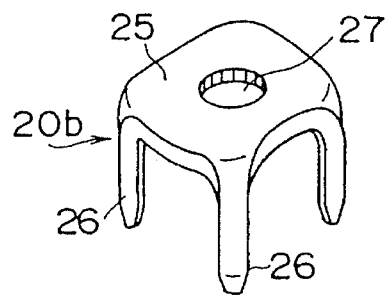
FIG. 5 is a view showing another variation of the shape of a vertebra plate.

The vertebra plates 20 are, as shown in FIG. 2, mounted to the side surface of the vertebrae 21 via the vertebra screws 22. A vertebra plate 20, as shown in FIGS. 3 to 5, is formed from a metallic material, and includes a top plate 25, spikes 26 which protrude from each corner of the top plate, and a hole or holes 27 provided in the top plate 25.

Figure 3:
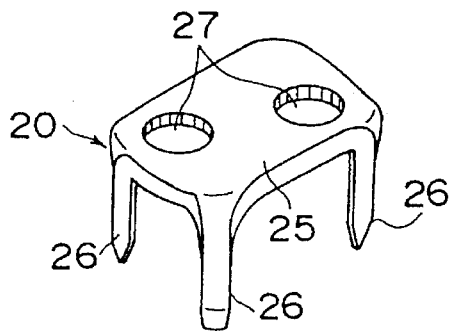
FIG. 3 is a perspective view of a vertebra plate.

The vertebra plate 20 shown in FIG. 3 has two holes 27 provided in its top plate 25, the two holes being positioned along a diagonal of the top plate 25 which is higher at the left side as viewed. The vertebra plate 20a shown in FIG. 4 has two holes 27 provided in its top plate 25, but these two holes 27 are located on a diagonal of the top plate that has an direction of inclination that is different from that in the case of FIG. 3. The vertebra plate 20b shown in FIG. 5 has one hole 27 provided in its top plate 25.

Figure 6:
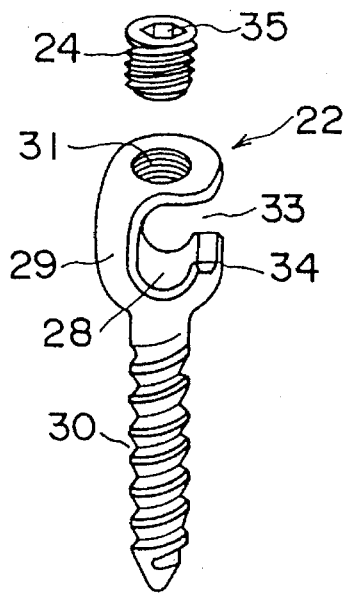
FIG. 6 is an exploded perspective view of a vertebra screw.

The vertebra screw. 22, as shown in FIG. 6, has a head 29 in which is provided a rod passage hole 28, and a threaded part 30 formed integral with the head 29, a set-screw 24 being screwed into a screw hole 31 which extends from top surface of the head 29 to the rod passage hole 28, thereby holding the rod 23 to the vertebra screw 22. The rod passage hole 28 provided in the head 29 has an opening 33 which is formed by cutting away part of the side of the head 29. This opening 33 is of a width that allows easy insertion of the rod 23 into the rod passage hole 28. The bottom part of the opening 33 has a jaw 34 formed in it to prevent the rod 23 from jumping out of the rod passage hole 28. If the set-screw 24 is, as shown in FIG. 7, screwed into the screw hole 31 beforehand to the extent that it does not interfere with the opening 33 provided in the head 29, it is not necessary to screw the set-screw 24 into the screw hole 31 when fixing the rod 23 to the vertebra plate.

Figure 7:
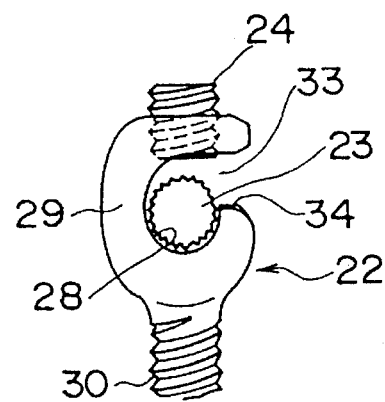
FIG. 7 is a view which shows a head part of a vertebra screw.
Figure 8:
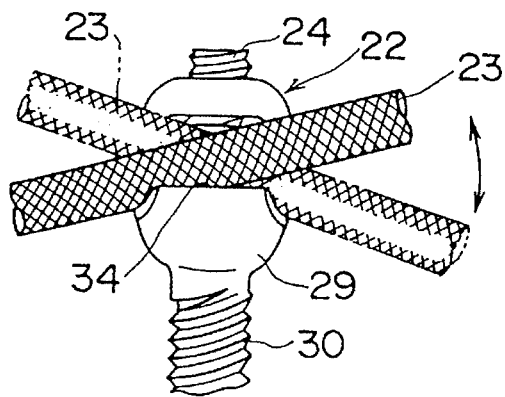
FIG. 8 is a view which shows the movement of a rod inserted into the head of the vertebra screw.
Figure 9:
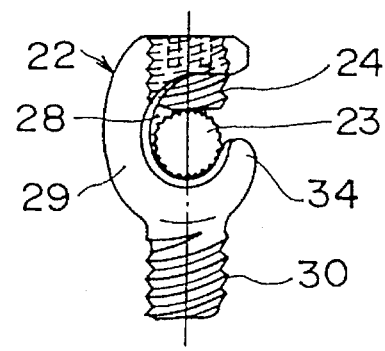
FIG. 9 is a view which shows the relative position between the rod and a set-screw provided in the head of the vertebra screw.
Figure 10:
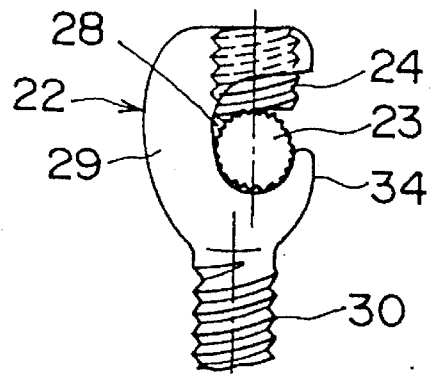
FIG. 10 is a view which shows a variation of the shape of a vertebra screw.
Figure 11:
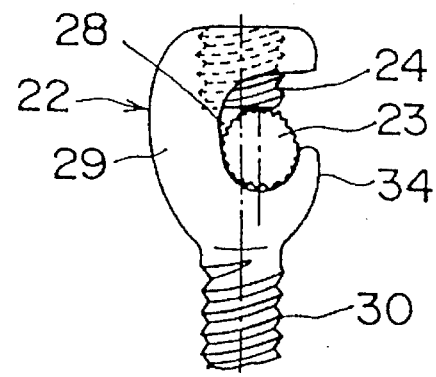
FIG. 11 is a view which shows another variation of the shape of a vertebra screw.

The rod passage hole 28 provided in the head 29, as shown in FIG. 7, is of a size that allows the rod 23 to be angled with respect to the axis of the rod within the rod passage hole 28 as shown in FIG. 8 when the set-screw 24 is lightly screwed into the screw hole 31, and the height of the jaw 34 is such that it is at a height of approximately the radius of the rod 23 which is placed on the bottom of the rod passage hole 28. In FIGS. 8 and 9, the axis of the set-screw 24 provided in the head 29 is aligned with the axis of the threaded part 30 of the vertebra screw. However, as shown in FIG. 10, it is possible to increase the thickness of the rear center part of the head 29 so that the axis of the center position of the rod passage hole 28 formed in the head 29 is offset from the axis of the threaded part 30, and it is also possible, as shown in FIG. 11 to make the axis of the set-screw 24 provided in the head 29 be aligned with the threaded part 30 while making the axis of the rod 23 offset from the axis of the threaded part 30 below it in the direction towards the opening side.

It is desirable to have the diameter of the set-screw 24 larger than the diameter of the rod. For example, the set-screw diameter is 7 mm for a rod diameter of 4 mm. By providing a hexagonal socket hole 35 in the head of the set-screw 24 (FIG. 6), it is possible to bury the set-screw 24 into the head 29 of the vertebra screw when screwing the set-screw into the screw hole 31.

Figure 12:
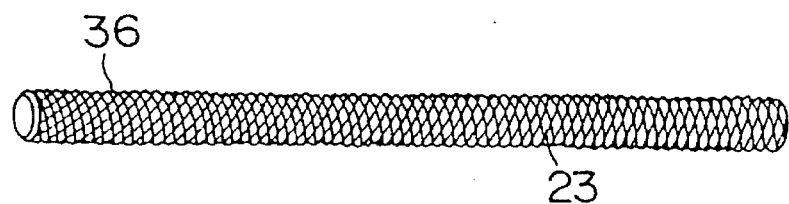
FIG. 12 is a perspective view of the rod.

The rod 23 is manufactured from a material such as stainless steel or titanium and, as shown in FIG. 12, has a diamond knurling pattern 36 applied to its entire outside surface. This diamond knurling pattern 36 provides unevenness in the surface of the rod 23, inhibiting it from slipping. Because the rods 23 can be made smaller in diameter than in a case of using a single rod, the construction is flexible, and has low rigidity.

FIGS. 13 through 16 show arrangements of vertebra plates which are mounted to the sides of vertebrae 21 of a patient having scoliosis via the vertebra screws 22. FIG. 13 shows an arrangement in which vertebra plates 20 are located at the side of each vertebra 21, in which case the rods 23 are held to the vertebra screws 22 which are located at the corners of parallelograms. FIG. 14 shows an arrangement in which vertebra plates 20 and vertebra plates 20a are located at the side of vertebrae 21, in which case the rods 23 are held to the vertebra screws 22 which are located at the corners of parallelograms and the vertebra screws 22 which are located at the corners of a trapezoid. FIG. 15 shows an arrangement in which the vertebra plates 20 and the vertebra plates 20a are located at the sides of vertebrae 21, in which case the rods 23 are held to the vertebra screws 22 which are located at the corners of parallelograms and to vertebra screws 22 which are located at the corners of a trapezoid, and further in which case one end of a rod 23 is held to a vertebra screw 22 of the vertebra plate 20b. The number of vertebra plates 20 and the number of vertebra plates 20a and 20b are determined by the condition of the vertebrae 21 of the scoliosis patient. FIG. 16 shows an arrangement in which vertebra plates 20b are located at the sides of vertebrae 21.

Next, a typical example of the use of an anterior correction instrument for scoliosis and the like according to the present invention to perform anterior correction of a scoliosis patient will be described.

First, spiked vertebra plates 20 and 20a are positioned at the sides of the vertebrae 21 of a scoliosis patient as shown in FIG. 1. In this case, the arrangement of the spiked vertebra plate 20 and spiked vertebra plates 20a is made as shown in FIG. 15, with a spiked vertebra plate 20b located at the end vertebra 21. This spiked vertebra plate 20b could be omitted.

Next, vertebra screws 22 are passed through the two holes 27 provided in the top plate of the vertebra plates 20 and 20a and through the hole 27 provided in the top plate of vertebra plate 20b and screwed into the vertebra 21, this causing the spikes 26 of the vertebra plates 20, 20a, and 20b to be buried into the vertebrae 21. When doing this, the vertebra screws 22 are aligned so that the openings 33 in the rod passage holes 29 all face either to the back or to the front of the patient's body.

Next, one rod 23 is formed by bending it so that its curvature is greater than the front-to-back curvature of each of the vertebrae 21 when viewed from the side of the vertebrae 21. This bent rod 23 is inserted into the openings 33 of the rod passage holes 28 in the heads 29 of the vertebra screws 22 of one of the rows of vertebra screws. By tightening the set-screws 24 into the screw holes 31 in the heads 29 of the vertebra screws lightly against the rod 23 inside the rod passage holes 28, the rod 23 is temporarily held in place within the rod passage holes 28. By doing this, the front-to-back curvature of the vertebrae of the scoliosis patient becomes larger than that before the rod 23 is inserted into the rod passage holes 28, but the vertebrae 21 are held in a condition in which they are laterally held along a straight line.

After completing the insertion of the rod 23 into the rod passage holes 28, the rod 23 is swung from this condition by approximately 90 degrees in the direction of either the patient's back or the patient abdomen. By swinging the rod 23 through approximately 90 degrees, the curvature direction of the rod 23 also is rotated by approximately 90 degrees, so that when viewed from the side of the vertebrae the front-to-back curvature of the vertebrae is straightened, with a large curvature appearing in the left-to-right direction.

Figure 17:
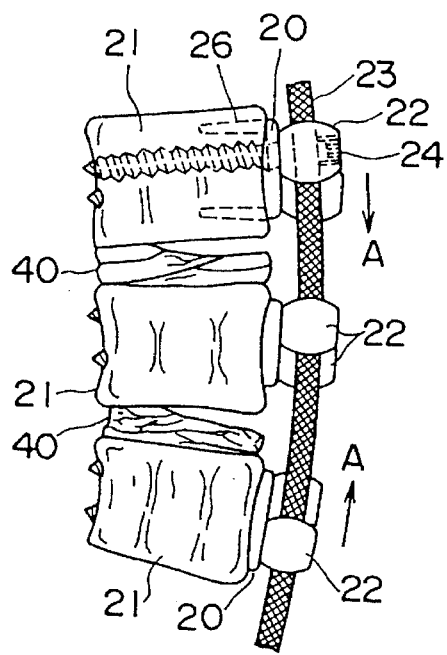
FIG. 17 is a view which shows a correction step in the anterior correction instrument for scoliosis or the like according to the present invention.

Next, as shown in FIG. 17, a bone transplant 40 is inserted between the curved vertebrae 21 so as to increase the spacing between the vertebra on the side opposite the rod 23. Then, the vertebra screws 22 are moved in the directions of the arrows A in FIG. 17 so that the spacing between the vertebrae is made narrow, whereupon the rod 23 which was inserted into the rod passage holes 28 is fixedly held to the heads 29 of the vertebra screws 22 by tightening the set-screws 24. In this manner, by inserting a thick bone transplant 40 on the inner side of the curvature, the vertebrae 21 are easily corrected to a straight line laterally, this completes the temporary front-to-back and left-to-right correction.

Figure 18:
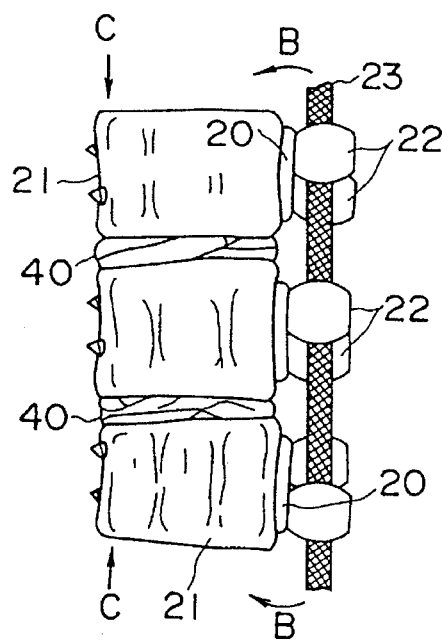
FIG. 18 is a view which shows the arrangement of vertebrae of a scoliosis patient after correction.

After the correction of the left-to-right direction curvature, the second rod 23 is inserted into the openings 33 of the rod passage holes 28 in the heads of the vertebra screws 22 of the other row. When this is done, because with the vertebrae 21 aligned in a straight line it is possible to insert the second rods 23 in a straight line. However, it could be curved as was done with the first rod 23, this second rod being curved in the left-right direction and inserted into the openings 33 and passed through the rod passage holes 28 in the screw heads 29 of the other row. The vertebrae 21 are then finely adjusted in the direction of the above-noted arrows A, while the elastic force B of the rod 23 applies force in the direction of the arrow C in FIG. 18 to the bone transplants 40 between vertebrae 21. Thereafter the second rod 23 which were inserted and passed through the rod passage holes 28 is held to the heads 29 of the vertebra screws 22 by means of the set-screws 24. By doing this, the vertebrae of the corrected scoliosis patient assume the condition as shown in FIG. 18.

In the case in which the anterior correction instrument according to the present invention is used for surgical treatment of such conditions as spinal damage, a comminuted fracture, or an osteoma, a pair of spiked vertebra plates 20 are located, in a manner similar to the case shown in FIG. 19, at the sides of normal vertebrae 11 and 12 at opposite ends of the damaged or chipped vertebra 10, and the fixing of the vertebra plates 20 to the normal vertebrae 11 and 12 is performed by screwing the vertebra screws 22 into the normal vertebrae 11 and 12 through the two holes provided in the top plate of the vertebra plates 1 and 2. The positioning of the vertebra plates 20 is performed by passing the rods 23 through the rod passage holes 28 in the heads 29 of the vertebra screws 22 which are screwed into the normal vertebrae 11 and 12, each of these rods 23 being held to the heads 29 of the vertebra screws 22 by means of the set-screws 24.

The treatment of a patient who has sustained vertebral damage or chipping due to an accident or tumor is performed by removing the vertebra 10 and intervertebral disc which sustained the damage or chipping and by inserting in its place a bone transplant or ceramic bone.

As described above, the present invention is capable of correcting front-to-back and lateral curvature of vertebrae by passing rods through rod passage holes provided in part of the vertebra screws which are screwed into the sides of vertebrae and by fixing the rods inside the rod passage holes. By providing a jaw on the opening of the head of each vertebra screw, it is possible to prevent the rod from jumping out of the rod passage hole even if it is rotated within the rod passage hole. Further, by offsetting the axis of the rod located within the rod passage hole from the axis of the threaded shank of the screw, and by making the diameter of the set-screw larger than the diameter of the rod, the rod can be securely fixed within the rod passage hole.

What is claimed is:

1. A vertebra screw device comprising:

a vertebra screw having a threaded part and a head, the threaded part being adapted for screwing into a vertebra, the threaded part having a central longitudinal axis, the head having a rod passage hole extending across the central longitudinal axis of the threaded part, a rod passing through the rod passage hole and having a central longitudinal axis, the head being generally C-shaped to define said rod passage hole therein and having four portions, the four portions being a top portion, a rear-center portion, a bottom portion, and a jaw portion, the top portion being opposite the bottom portion, the rear-center portion being connected to the top and bottom portions, the jaw portion being connected to the bottom portion, the jaw portion being separated from the top portion by an opening, the jaw portion being closer than the bottom portion to the top portion, the rear-center portion being opposite the opening, the opening being adapted to allow insertion of the rod through the opening and into the rod passage hole, the vertebra screw having a holding means for fixedly holding the rod in the rod-passage hole where the rod is in contact with substantially the entire jaw portion, the head and the rod-passage hole being configured to substantially snugly receive the rod in the rod-passage hole such that the central longitudinal axis of the rod does not intersect with, and is offset toward and contacting substantially the entire jaw portion relative to the central longitudinal axis of the threaded part.

2. A vertebra screw device as claimed in claim 1, wherein the rear-center portion is thicker than the jaw portion.

3. A vertebra screw device as claimed in claim 1, wherein the holding means comprises a screw hole in top portion of the head and a secondary screw screwed into the screw hole, the secondary screw having a portion protruding into the rod-passage hole, the protruding portion holding the rod having a diameter against a wall of the bottom portion; the secondary screw having a central longitudinal axis that aligns with the central longitudinal axis of the threaded part of the vertebra screw.

4. A vertebra screw device as claimed in claim 1, wherein the holding means comprises a screw hole in the head and a secondary screw screwed into the screw hole, the secondary screw having a portion protruding into the rod-passage hole, the protruding portion holding the rod having a diameter against a wall of the bottom portion, the screw hole having a central longitudinal axis that is offset from the central longitudinal axis of the rod.

5. A vertebra screw device as claimed in claim 1, wherein the holding means comprises a screw hole in the top portion of the head and a secondary screw screwed into the screw hole, the secondary screw having a portion protruding into the rod-passage hole, the protruding portion having a diameter and holding the rod having a diameter against a wall of the bottom portion, the diameter of the protruding portion being larger than the diameter of the rod.

6. A vertebra screw device as claimed in claim 1, wherein the opening is positioned such that a plane can bisect the opening without intersecting the top portion or the bottom portion, the plane being perpendicular to the central longitudinal axis of the threaded part.

7. A screw device of claim 1, the screw device further comprising a plurality of said screw devices and a plurality of vertebra plates.

8. A screw device of claim 1, the screw device further comprising a plurality of said screw devices and a plurality of vertebra plates, each vertebra plate having a top plate with a hole, the threaded part of the screw device being inserted through the hole.

9. A screw device of claim 2, the screw device further comprising a plurality of said screw devices and a plurality of vertebra plates.

10. A screw device of claim 3, the screw device further comprising a plurality of said screw devices and a plurality of vertebra plates.

11. A screw device of claim 4, the screw device further comprising a plurality of said screw devices and a plurality of vertebra plates.

12. A screw device of claim 5, the screw device further comprising a plurality of said screw devices and a plurality of vertebra plates.

13. A screw device of claim 6, the screw device further comprising a plurality of said screw devices and a plurality of vertebra plates.

14. A vertebra screw device according to claim 1 wherein the rear-center portion is thicker than the jaw portion.

15. A vertebra screw as claimed in claim 1, wherein the holding means comprises a single screw hole in the top portion of the head and a single secondary screw screwed into the screw hole, the secondary screw having a portion protruding into the rod passage hole, the protruding portion holding the rod having a diameter against a wall of the bottom portion, the secondary screw having a central longitudinal axis that aligns with the central longitudinal axis with the threaded part of the vertebra screw.

* * * * *